United States Patent
Burr et al.

(10) Patent No.: US 10,124,128 B2
(45) Date of Patent: Nov. 13, 2018

(54) AEROSOLIZATION APPARATUS WITH REMOVABLE MOUTHPIECE

(75) Inventors: John D. Burr, Redwood City, CA (US); Jeff R. Wood, Mountain View, CA (US); Adrian E. Smith, Belmont, CA (US); John A. Howard, Palo Alto, CA (US); Fabrizio Niccolai, Milan (IT)

(73) Assignee: BGP Products Operations GmbH (CH)

( * ) Notice: Subject to any disclaimer, the term of this patent is extended or adjusted under 35 U.S.C. 154(b) by 512 days.

(21) Appl. No.: 10/298,177

(22) Filed: Nov. 14, 2002

(65) Prior Publication Data

US 2003/0150454 A1      Aug. 14, 2003

Related U.S. Application Data (60) Provisional application No. 60/336,320, filed on Nov. 14, 2001.

(51) Int. Cl.
*A61M 15/08* (2006.01)
*A61M 15/00* (2006.01)

(52) U.S. Cl.
CPC ...... *A61M 15/0028* (2013.01); *A61M 15/003* (2014.02); *A61M 15/08* (2013.01);
(Continued)

(58) Field of Classification Search
USPC ............... 128/203.12, 203.15, 20.21
See application file for complete search history.

(56) References Cited

U.S. PATENT DOCUMENTS

| 154,864 A | * | 9/1874 | Harvey | 411/411 |
| 3,906,950 A | * | 9/1975 | Cocozza | 128/203.15 |

(Continued)

FOREIGN PATENT DOCUMENTS

| EP | 0753319 | 1/1997 |
| WO | 95/03846 | 2/1995 |

(Continued)

OTHER PUBLICATIONS

Meakin et al., "Drug Emission Efficacy of Turbospin® A New Single Dose Dry Powder Inhaler", $14^{th}$ Pharmaceutical Technology Conference, Barcelona—Spain, Apr. 4, 5, and 6, 1995.

*Primary Examiner* — Katherine M Shi
*Assistant Examiner* — Michael Mendoza (57) ABSTRACT

An aerosolization apparatus comprises a body having an inlet, an endpiece having an outlet, the endpiece being connectable to the body to define a chamber, wherein the chamber is sized to receive a capsule containing a pharmaceutical formulation in a manner which allows the capsule to move within the chamber. The apparatus further includes a connection mechanism to provide selective connection of the endpiece to the body, wherein a rotational force between the endpiece and the body is needed to connect or disconnect the endpiece from the body, the rotational force being applied about an axis passing through the chamber. When a user inhales, air enters into the chamber through the inlet so that the pharmaceutical formulation is aerosolized within the chamber and the aerosolized pharmaceutical formulation is delivered to the user through the outlet. The connection mechanism prevents inadvertent disconnection of the endpiece from the body.

35 Claims, 5 Drawing Sheets

(52) U.S. Cl.
CPC . *A61M 2202/064* (2013.01); *A61M 2202/206* (2013.01); *A61M 2210/0618* (2013.01); *A61M 2210/0625* (2013.01)

(56) References Cited

U.S. PATENT DOCUMENTS

| | | | |
|---|---|---|---|
| 3,991,761 A | 11/1976 | Cocozza | |
| 4,069,819 A | 1/1978 | Valentini et al. | |
| 4,161,516 A | 7/1979 | Bell | |
| 4,249,526 A * | 2/1981 | Dean et al. | 128/203.15 |
| 4,641,644 A | 2/1987 | Andersson et al. | |
| 4,995,385 A * | 2/1991 | Valentini et al. | 128/203.21 |
| 5,301,666 A * | 4/1994 | Lerk et al. | 128/203.15 |
| 5,331,954 A | 7/1994 | Rex et al. | |
| 5,379,763 A * | 1/1995 | Martin | 128/203.15 |
| 5,447,151 A | 9/1995 | Brunet et al. | |
| 5,505,194 A | 4/1996 | Adjei et al. | |
| 5,699,789 A | 12/1997 | Hendricks | |
| 5,727,546 A | 3/1998 | Clarke et al. | |
| 5,797,391 A | 8/1998 | Cook et al. | |
| 5,901,703 A * | 5/1999 | Ohki et al. | 128/203.12 |
| D410,541 S | 6/1999 | Moulin | |
| 5,921,236 A * | 7/1999 | Ohki et al. | 128/203.15 |
| 5,989,217 A | 11/1999 | Ishizeki et al. | |
| D420,736 S | 2/2000 | Moulin | |
| 6,230,707 B1 | 5/2001 | Hörlin | |
| 6,298,846 B1 * | 10/2001 | Ohki et al. | 128/203.15 |
| 6,470,884 B2 * | 10/2002 | Horlin | 128/203.15 |
| 6,705,313 B2 * | 3/2004 | Niccolai | 128/203.21 |
| 6,732,732 B2 * | 5/2004 | Edwards et al. | 128/203.21 |
| 6,766,799 B2 * | 7/2004 | Edwards et al. | 128/203.15 |

FOREIGN PATENT DOCUMENTS

| | | |
|---|---|---|
| WO | 97/27892 | 8/1997 |
| WO | 97/42992 | 11/1997 |
| WO | 99/45987 | 9/1999 |
| WO | 02/083220 | 10/2002 |

* cited by examiner

AEROSOLIZATION APPARATUS WITH REMOVABLE MOUTHPIECE

RELATED APPLICATIONS

The present application claims the benefit of U.S. Provisional Application No. 60/336,320 filed on Nov. 14, 2001.

BACKGROUND

The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before they can be effectively absorbed by the body. Inhaleable drug delivery, where an aerosolized pharmaceutical formulation is orally or nasally inhaled by a patient to deliver the formulation to the patient's respiratory tract, has proven to be a particularly effective and/or desirable alternative. For example, in one inhalation technique, a pharmaceutical formulation is delivered deep within a patient's lungs where it may be absorbed into the blood stream. Many types of inhalation devices exist including devices that aerosolize a dry powder, devices comprising a pharmaceutical formulation stored in or with an inhaleable propellant, devices which use a compressed gas to aerosolize a liquid pharmaceutical formulation, and similar devices.

In one dry powder aerosolization technique, a capsule containing an inhaleable dry powder is loaded into a chamber in an aerosolization device. Within the chamber, the dry powder is at least partially emptied and dispersed to aerosolize the dry powder so that it may be inhaled by a patient. However, in conventional devices, the manner of accessing the chamber may often lead to device inconsistencies and/or failures. Also, the dry powder in the cavity can cause the access mechanism to become less effective at efficiently opening and closing.

Therefore, it is desirable to improve the manner of accessing an aerosolization device chamber. It is further desirable to access the chamber in a manner that reduces device inconsistencies and/or failures. It is still further desirable to access the cavity so that debris in the cavity will have reduced adverse affects on the functioning of the device.

SUMMARY

The present invention satisfies these needs. In one aspect of the invention an aerosolization apparatus comprises a body and an endpiece, the body and endpiece being connectable to one another by a connection mechanism that prevents inadvertent disconnection of the parts.

In another aspect of the invention, an aerosolization apparatus comprises a body having an inlet, an endpiece having an outlet, the endpiece being connectable to the body to define a chamber, wherein the chamber is sized to receive a capsule containing a pharmaceutical formulation in a manner which allows the capsule to move within the chamber, a connection mechanism to provide selective connection of the endpiece to the body, wherein a rotational force between the endpiece and the body is needed to connect or disconnect the endpiece from the body, the rotational force being applied about an axis passing through the chamber, and a puncturing mechanism capable of providing an opening in the capsule, whereby when a user inhales, air enters into the chamber through the inlet so that the pharmaceutical formulation is aerosolized within the chamber and the aerosolized pharmaceutical formulation is delivered to the user through the outlet.

In another aspect of the invention, an aerosolization apparatus comprises a body having an inlet, an endpiece having an outlet, the endpiece being connectable to the body to define a chamber, wherein the chamber is sized to receive a capsule containing a pharmaceutical formulation in a manner which allows the capsule to move within the chamber, a connection mechanism to provide selective connection of the endpiece to the body, wherein the connection mechanism comprises engageable threads, and a puncturing mechanism capable of providing an opening in the capsule, whereby when a user inhales, air enters into the chamber through the inlet so that the pharmaceutical formulation is aerosolized within the chamber and the aerosolized pharmaceutical formulation is delivered to the user through the outlet.

In another aspect of the invention, an aerosolization apparatus comprises a body having an inlet, an endpiece having an outlet, the endpiece being connectable to the body to define a chamber, wherein the chamber is sized to receive a capsule containing a pharmaceutical formulation in a manner which allows the capsule to move within the chamber, a connection mechanism to provide selective connection of the endpiece to the body, wherein the connection mechanism comprises a protrusion that is receivable within a slot, the slot comprising a longitudinally extending portion and a transversely extending portion, and a puncturing mechanism capable of providing an opening in the capsule, whereby during inhalation air enters into the chamber through the inlet so that the pharmaceutical formulation is aerosolized within the chamber and the aerosolized pharmaceutical formulation is delivered to the user through the outlet.

In another aspect of the invention, a method of providing an aerosolized pharmaceutical formulation comprises providing a body and an endpiece, the endpiece being connectable to the body when a rotational force is applied thereto to define a chamber, the chamber being sized to receive a capsule containing a pharmaceutical formulation, wherein the rotation force is applied about an axis that passes through the chamber, and aerosolizing the pharmaceutical formulation when a user inhales by causing air to flow through an inlet in the body, within the chamber, and through an outlet in the endpiece to provide the aerosolized pharmaceutical formulation to the user.

In another aspect of the invention, a method of aerosolizing a pharmaceutical formulation comprises inserting a capsule containing a pharmaceutical formulation into a chamber in a body, rotating an endpiece relative to the body to connect the endpiece to the body, the rotation being about an axis passing through the chamber, before, during, or after inserting the capsule into the chamber, providing an opening in the capsule, and inhaling through an opening in the endpiece to cause air to flow into the chamber through an inlet in the body thereby aerosolizing the pharmaceutical formulation.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

FIG. 6C is a schematic sectional side view of the version of the aerosolization device of FIG. 6A in a connected configuration;

FIGS. 7A and 7B are schematic sectional and schematic perspective views, respectively, of a portion of another version of an aerosolization device;

FIG. 8 is a schematic perspective view of a portion of another version of an aerosolization device;

FIG. 9 is a schematic side view of a body of a version of an aerosolization device;

FIG. 10 is a schematic sectional side view of a body of another version of an aerosolization device; and FIGS. 11A though 11M illustrate parts of a specific version of an aerosolization device.

DESCRIPTION

The present invention relates to delivering an aerosolized pharmaceutical formulation to a patient. Although the process is illustrated in the context of aerosolizing a dry powder pharmaceutical formulation, the present invention can be used in other processes and should not be limited to the examples provided herein.

An aerosolization device 100 of the present invention is shown schematically in FIG. 1. The aerosolization device 100 includes a body 105 and an endpiece 110 that may be attached to the body 105 to form a chamber 115 within the interior of the body 105 and the endpiece 110. The endpiece 110 includes an end 120 defining an outlet 125. The end 120 may be sized and shaped to be received in a user's mouth. Alternatively, the end 120 may be sized and shaped to be received in a nostril of a user or may sized and shaped to be received by a mask, a spacer chamber, a respirator circuit, or the like. The body includes one or more inlets 130 in communication with the chamber 115. Together the inlets 130, the chamber 115, and the outlet 125 define an airway through the aerosolization device 100. Accordingly, when a user contacts the endpiece 110 and inhales or otherwise creates a vacuum at the outlet 125, a pharmaceutical formulation with the chamber 115 may be delivered to the user through the outlet 125. In one version, the pharmaceutical formulation may be contained within a capsule that is positionable within the chamber 115, the chamber 115 being sized to receive the capsule in a manner which allows the capsule to move within the chamber 115. In this version, the endpiece 110 includes a perforated member 135 having one or more openings 140 therein. The perforated member 135 sufficiently blocks the chamber 115 to retain a capsule in the chamber 115, while the openings 140 allow air and/or other material to pass to the outlet 125. A connection mechanism 150 may be provided to allow the endpiece 110 to be attached to the body 105.

In one version, as shown in FIG. 2, the connection mechanism 150 may allow the body 105 and the endpiece 110 to be disconnected to allow for access to the chamber 115. In this version, the endpiece 110 may be disconnected from the body 105 to allow a pharmaceutical formulation to be inserted into the chamber, for example by allowing a capsule to be inserted into the chamber 115. In this version, the connection mechanism includes a body connection member 150*a*that cooperates with an endpiece connection member 150*b* to selectively connect and disconnect the endpiece 110 to the body 105.

After a capsule 160 has been inserted into the chamber 115, the endpiece 110 may again be attached to the body 105 to secure the capsule 160 within the chamber 115, as shown in FIG. 3. The capsule 160 is opened, for example by puncturing the capsule 160 prior to insertion or within the chamber 115, such as by longitudinally advancing a sliding puncture mechanism 162. When opened, the pharmaceutical formulation in the capsule is allowed to exit the capsule 160. In one version, the pharmaceutical formulation is in a dry powder form and the flow of air through the airway causes the pharmaceutical formulation to be aerosolized. For example, as shown in FIG. 3, a user may contact the endpiece 110 with his or her mouth and inhale, thereby drawing air through the outlet 125, as shown by arrow 165. This inhalation causes air to be taken in through the inlets 130, as shown by arrows 170. The air taken in causes the capsule 160 to agitate within the chamber 115. The agitation causes the dry powder pharmaceutical formulation to leave the capsule 160 and become aerosolized in the airway. The aerosolized pharmaceutical formulation passes through the perforated member 135 and is delivered to the user where it may be inhaled to a position in the user's respiratory tract. In one particular embodiment, a plurality of inlets 130 may be designed to cause the inlet air 170 to swirl within the chamber, for example, by being at least partially tangentially oriented as described in U.S. Pat. Nos. 4,995,385 and 4,069,819, both of which are incorporated herein by reference in their entireties. In such an arrangement, the chamber 115 comprises a longitudinal axis that lies generally in the inhalation direction 165, and the capsule 160 is insertable lengthwise into the chamber 115 so that the capsule's longitudinal axis may be parallel to the longitudinal axis of the chamber 115. The swirling air flow then causes the capsule to rotate within the chamber 115 in a manner where the longitudinal axis of the capsule is remains at an angle less than 80 degrees, and preferably less than 45 degrees from the longitudinal axis of the chamber. In one version, this rotation is caused by the width of the chamber being less than the length of the capsule.

Often, a user will grasp the body 105 during use while inhaling through the endpiece 110. It has been discovered that doing so may create a disconnection force in the inhalation direction 165 between the body 105 and the endpiece 110. Accordingly, the connection mechanism 150 may be designed to prevent undesired disconnection of the endpiece 110 from the body 105 during use.

In one version, the connection mechanism 150 requires a force to be applied at least partially in a direction other than in an inhalation direction 165 in order to disconnect the endpiece 110 from the body 105. Thus, in this version, the user's inadvertent forcing apart of the endpiece 110 and the body 105 during use does not generate a force in the direction required for disconnection. For example, the force required for disconnection may be a rotational force. In one particularly preferred version, the rotational force is a rotational force applied about an axis that passes through the chamber. For example, the rotational force may be applied about an axis that passes through the chamber and is parallel or coaxial with a longitudinal axis passing through the chamber. Such a rotational force is generally not generated by a user during inhalation making inadvertent disconnection more difficult. Examples of connection mechanisms of this type are schematically shown in FIGS. 4-10.

Figure 1:
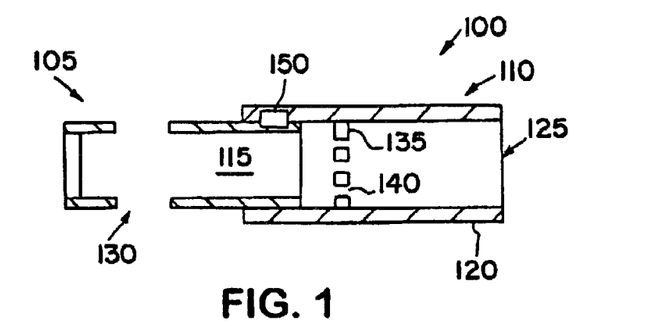
FIG. 1 is a schematic sectional side view of a version of an aerosolization device of the invention with an endpiece and body connected.
Figure 2:
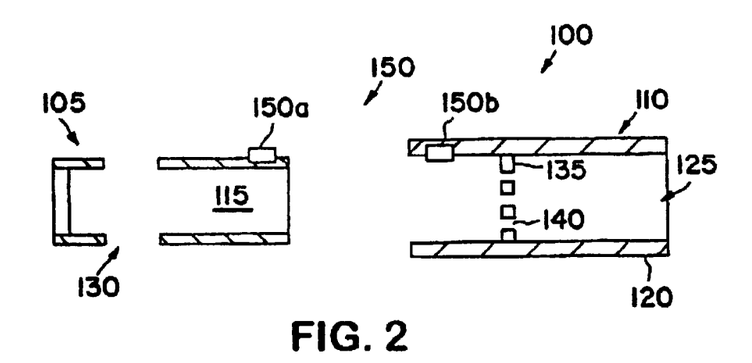
FIG. 2 is a schematic sectional side view of the version of an aerosolization device of FIG. 1 with the endpiece and body disconnected.
Figure 3:
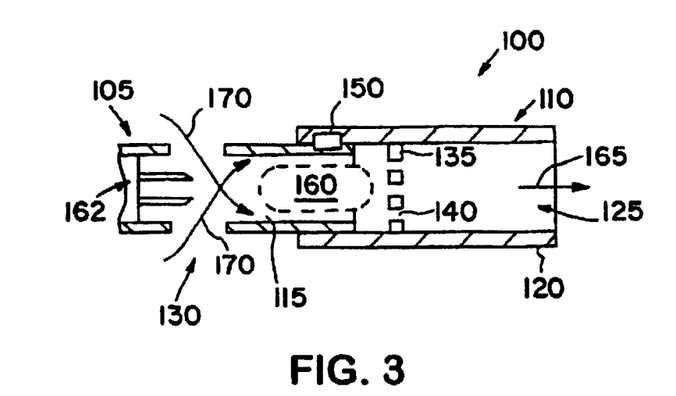
FIG. 3 is a schematic sectional side view of a version of an aerosolization device in use.
Figure 4A:
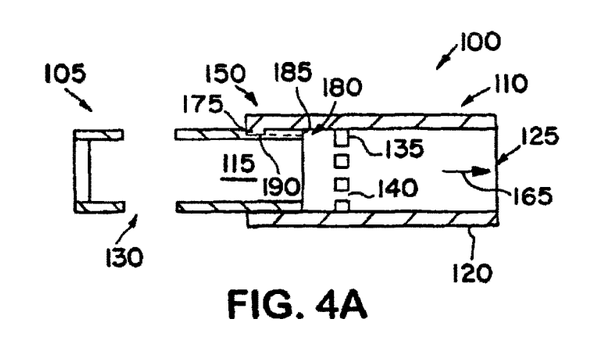
FIG. 4A is a schematic sectional side view of another version of an aerosolization device.
Figures 4B, 5C:
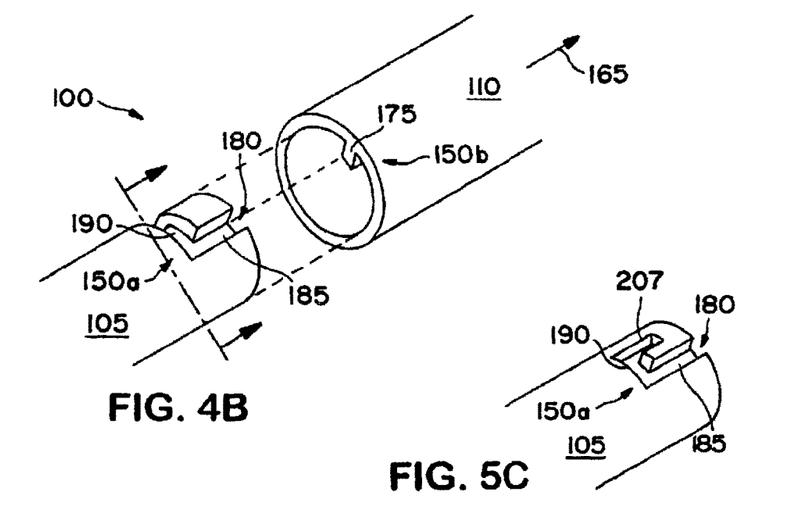
FIG. 4B is a schematic prospective view of the aerosolization device of FIG. 4A.
FIGS. 5A through 5C are schematic views of versions of connection mechanisms for use with an aerosolization device.
Figure 4C:
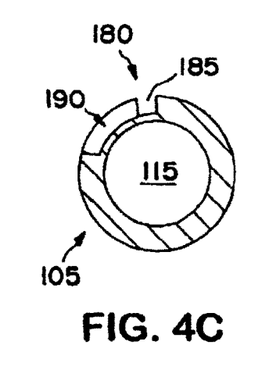
FIG. 4C is a schematic section view along section A-A in FIG. 4B.
Figure 5A:
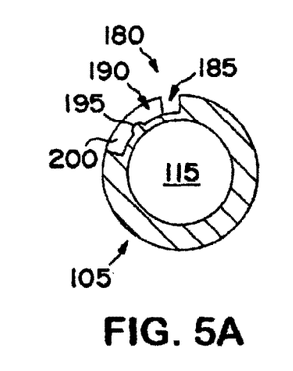
Figure 5B:
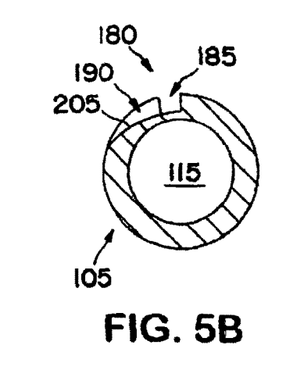
Figure 6A:
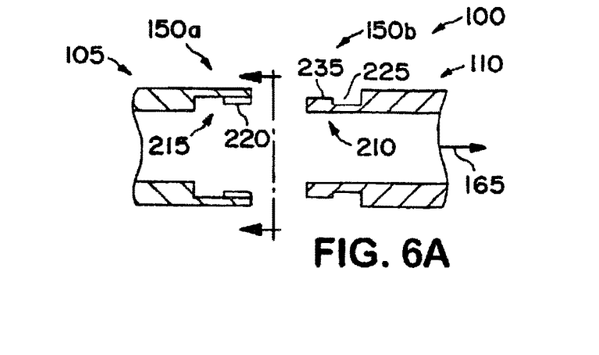
FIG. 6A is a schematic sectional side view of a portion of another version of an aerosolization device.
Figure 6B:
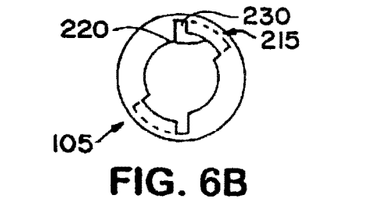
FIG. 6B is a schematic end view of the body of the version of an aerosolization device of FIG. 6A.
Figure 6C:
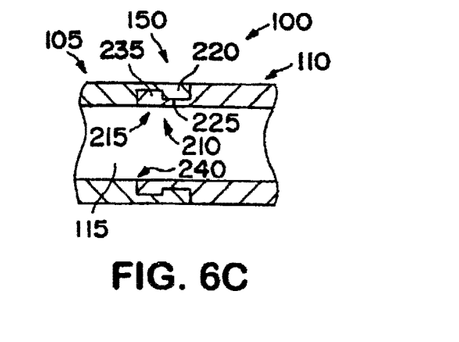
Figure 7A:
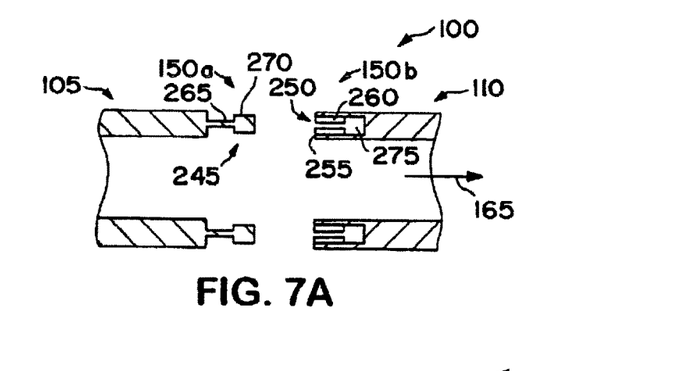
Figure 7B:
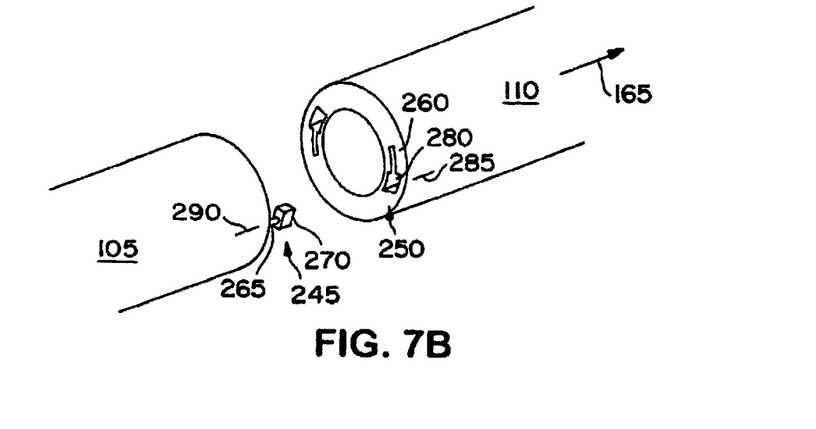

In the version of FIGS. 4A, 4B, and 4C the aerosolization device 100 comprises a connection mechanism 150 including a protrusion 175 on the endpiece 110 and a groove or slot 180 on the body 105. Alternatively, the protrusion 175 may be provided on the body 105 and the slot 180 may be provided on the endpiece 110. The protrusion 175 is insertable into the slot 180 for attachment of the endpiece 110 to the body 105. For example, in the version shown, the slot 180 may comprise a longitudinally extending portion 185 and a transversely extending portion 190. To connect the parts, the protrusion 175 is inserted into the longitudinally extending portion 185 until it is in a position in alignment with the transversely extending portion 190 at which time the endpiece 110 is twisted relative to the body 105 to cause the protrusion 175 to slide within the transversely extending portion 190. When the protrusion 175 is within the transversely extending portion 190, the walls of the transversely extending portion 190 prevent movement of the protrusion 175, and thus movement of the endpiece 110 in the inhalation direction 165. Accordingly, when the user inhales on the endpiece 110, the endpiece 110 is prevented from disconnecting with the body 105 as a result of forces in the inhalation direction 165 alone. FIG. 4C is a cross-section along line A-A of the transversely extending portion 190. As shown, the transversely extending portion 190 extends partly around the circumference of the body 105. Alternatively, the transversely extending portion 190 may extend completely around the body 105 or to a different circumferential position than the position shown.

The slot 180 may further be designed to help secure the protrusion 175 within the slot 180. For example, as shown in FIGS. 5A, 5B, and 5C, the transversely extending portion 190 may include a member which serves to secure the protrusion 175 within the transversely extending portion 190. In the version of FIG. 5A, a projection 195 such as a bump is provided on the base of the transversely extending portion 190. When sufficient rotational force is applied, the protrusion 175 may slide over the projection 195 to be positioned in a secured position 200 in the slot 180, thereby providing a snap fit. To disconnect the parts, the endpiece 110 may be twisted in the opposite direction with sufficient force to cause the protrusion 175 to again slide past the projection 195. Additionally or alternatively, one or more projections 195 may be provided on the side walls of the transversely extending portion 190. In the version of FIG. 5B, the depth of the base 205 of the transversely extending portion 190 gradually lessens. Accordingly, as the protrusion 175 is slid in the transversely extending portion 190, the frictional forces increase and the protrusion 175 may be wedged into a secure position within the slot 180. To disconnect this version, a sufficient force is applied to overcome the wedging of the protrusion 175 in the transversely extending portion 190. Alternatively, the side walls of the transversely extending portion may be somewhat V-shaped to create the wedging effect. In the version shown in FIG. 5C, the slot 180 comprises a second longitudinally extending portion 207 spaced from the longitudinally extending portion 185 and communicable therewith by the transversely extending portion 190. When in the forward region of the second longitudinally extending portion 207, the protrusion 175 is prevented from movement in the transverse direction and from movement in the inhalation direction 165. Thus, force generated during inhalation does not cause disconnection. To disconnect, the endpiece is moved in a direction opposite to the inhalation direction 165. A projection or a wedging surface, as discussed above, may be further provided in the second longitudinally extending portion 207 to further secure the protrusion 175. Optionally, a biasing member, such as a compressed spring, may be positioned to bias the protrusion in the inhalation direction 165 when the protrusion is in the slot 180. The biasing member will serve to secure the protrusion in the second longitudinally extending portion 207 until the user applies a force sufficient to overcome the bias.

In another version, as shown for example in FIGS. 6A, 6B, and 6C, the aerosolization device 100 comprises a connection mechanism 150 with a longitudinally extending protrusion 210 that is receivable in an interior slot 215. In the version shown, the longitudinal protrusion 210 is provided on the endpiece 110 and the interior slot 215 is provided on the body 105. Alternatively, this may be reversed. The interior slot 215 includes a collar 220 which is receivable in a recess 225 on the protrusion 210 to prevent movement of the endpiece 110 in the inhalation direction 165 when the endpiece 110 is attached to the body 105, as shown in the connected configuration shown in FIG. 6C. A portion of the collar 220 is reduced in size or thinned to provide a longitudinal access 230 to the slot 215, as best shown in FIG. 6B which is an end view of the body 105 along line BB. To attach the endpiece 110 to the body 105 in this version, the protrusion 210 is inserted into the longitudinal access 230 of the slot 215 until the end portion 235 extends beyond the collar 220. The endpiece 110 is then twisted so that the end portion 235 is positioned behind the collar 220 and prevented from moving in the inhalation direction 165. A snap fit projection or a sloped wedging surface, as discussed above, may be provided in the slot 215 to further secure the protrusion 210 within the slot 215. Optionally, multiple protrusions and slots may be provided, as shown.

As can be seen in FIG. 6C, this version of the aerosolization device 100 also provides a substantially smooth surface 240 within the chamber 115. This smooth surface 240 may be advantageous in increasing the aerosolization space in the chamber 115 thereby creating more space in which a capsule may rattle. Additionally, the less discontinuous surface may provide more consistent rattling of the capsule and, thus, more consistent emptying of the capsule. FIGS. 7A and 7B show another version of a connection mechanism 150 that provides a smooth surface when in a connected configuration. In this version, a longitudinal protrusion 245 extends from the body 105 and is insertable into an opening 250 in the end surface 255 in the endpiece 110. Alternatively, the protrusion 245 and opening 250 may be reversed. The opening 250 includes a collar 260 that may be engaged around or near a recess 265 on the protrusion 245 when in a connected configuration to prevent the endpiece 110 from moving relative to the body 105 in the inhalation direction 165. To connect the parts, an end portion 270 of the protrusion 245 is inserted into the opening 250 at an enlarged area 280, as best shown in FIG. 7B. The parts are then rotated relative to one another so that the end portion 270 is secured within a cavity 275 beyond the collar 260. The cavity 275 may have snap fit projections or wedging surfaces, as discussed above, to further secure the protrusion 245 within the opening 250. Multiple protrusions 245 and openings 250 may be provided.

In the versions of FIGS. 4 through 7, indicia may be provided to aid the user when connecting or disconnecting the endpiece 110 to the body 105. For example, as shown in the version of FIG. 7B, a first marking 285 may be provided on the outer surface of the endpiece 110 and a second marking 290 may be provided on the outer surface of the body 105. When the first marking 285 and the second marking 290 are aligned with one another, the two parts may be disconnected. Additionally or alternatively, markings may be provided to indicate to the user in which direction to twist the parts in order to connect or to disconnect the parts.

Figure 8:
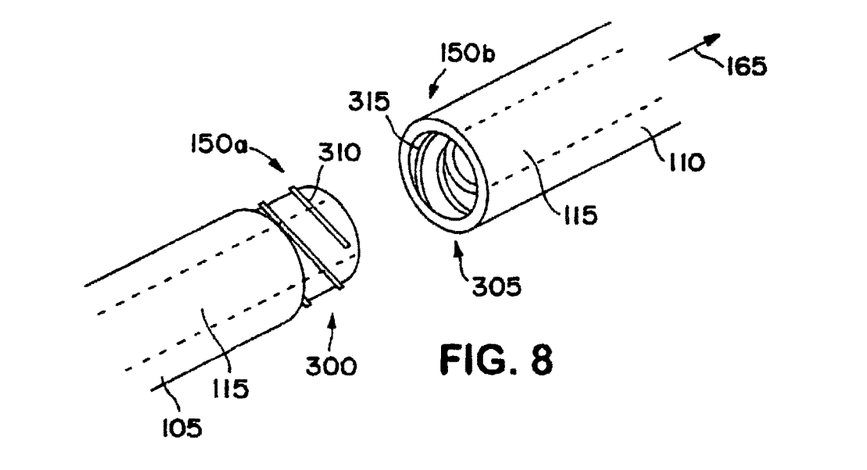

Another version of an aerosolization device 100 comprising a connection mechanism 150 that must at least partially be forced in a direction other than an inhalation direction 165 is shown in FIG. 8. In this version, the body 105 includes a male portion 300 that is insertable into a female portion 305 on the endpiece 110. On the male portion 300 are external threads 310 that may engage internal threads 315 on the endpiece 110. Accordingly, the endpiece 110 may be attached to the body 105 by screwing the parts together. The threaded engagement prevents the endpiece 110 from disconnecting from the body 105 when a force in the inhalation direction 165 is applied. It has been discovered that this arrangement prevents disconnection of the parts during inhalation by a user. Alternatively, the threaded arrangement shown in FIG. 8 may be switched so that the male portion 300 is on the endpiece 110 and the female portion 305 is on the body 105. The threads may be standard helical threads. Alternatively, the threads may comprise a series of bumps and/or posts that mate in a screw-like manner.

Figure 9:
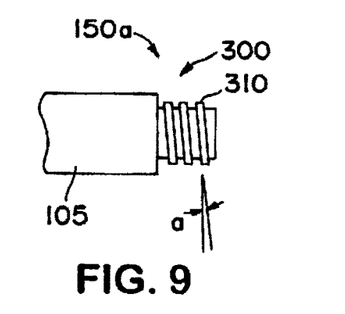
Figure 10:
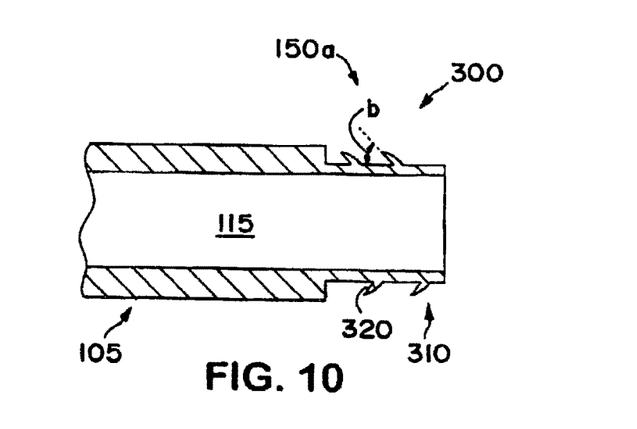

The thread arrangement may be designed to further prevent disconnection of the endpiece 110 from the body 105 during use. For example, FIG. 9 shows a version of a threaded portion having threads of high pitch. It has been determined that when the thread angle, a, is less than about 9 degrees, inhalation forces in the inhalation direction 165 are not sufficient to unscrew the parts. Accordingly, in one version, the threads have a thread angle of less than about 9 degrees, and more preferably less than about 7 degrees. Alternatively or additionally, the threads may be shaped to further prevent disconnection of the endpiece 110 and the body 105 when a force in the inhalation direction 165 is applied. For example, in the version shown in FIG. 10, the threads have a recessed backside 320 to provide interlocking of the threads and thereby preventing stripping of the threads when stressed. In one version, the recess angle, b, is less than 90 degrees, more preferably less than about 75 degrees, and most preferably less than about 60 degrees. The mating threads on the opposing part are shaped to be received in the recessed backside 320.

Figure 11A:
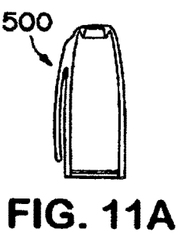
Figure 11B:
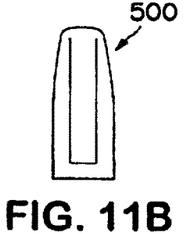
Figure 11C:
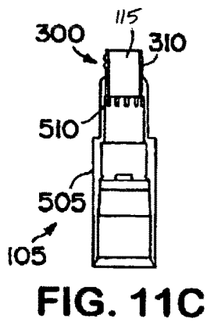
Figure 11D:
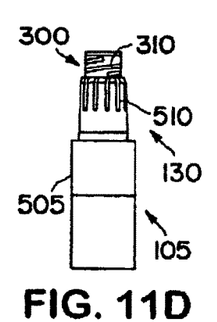
Figure 11E:
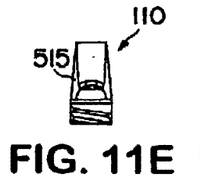
Figure 11F:
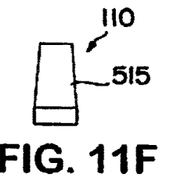
Figure 11G:
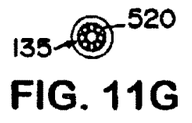

FIGS. 11A though 11M illustrate parts from a specific version of an aerosolization device 100. FIGS. 11A and 11B show, respectively, a sectional view and a side view of a cap 500 that may be inserted over an endpiece 110. FIGS. 11C and 11D show, respectively, a sectional view and a side view of a specific version 505 of a body 105. The version includes a plurality of angled slots 510 that provide an inlet 130 into the chamber 115. FIGS. 11E and 11F show, respectively, a sectional view and a side view of a version 515 of an endpiece 110. The endpiece 110 may be connected and disconnect to the body 105 by rotational force. FIG. 11G shows an end view of the endpiece 110 of FIG. 11E showing an arcuate version 520 of a perforated member 135 within the endpiece 110.

Figure 11H:
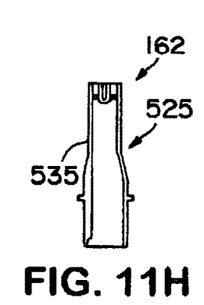
Figure 11I:
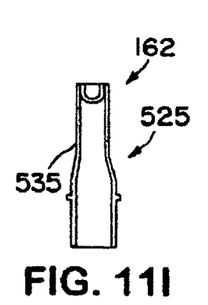
Figure 11J:
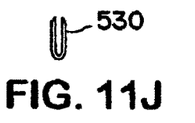
Figure 11K:
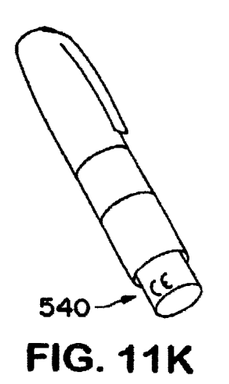
Figure 11L:
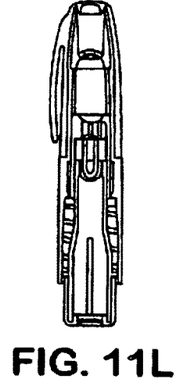
Figure 11M:
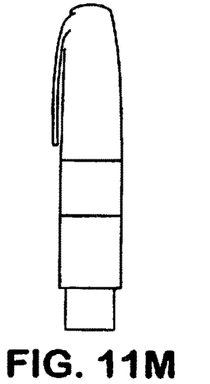

FIGS. 11H and 11I show, respectively, a version 525 of a puncturing mechanism 162. A U-shaped puncturing member 530, as shown in FIG. 11J, is seated in the end of a slidable member 535. As shown in FIG. 11K, a position 540 on the device may be used to provide a marking on the device. FIGS. 11L and 11K show, respectively, a sectional view and a side view of an assembled device according to the version of FIGS. 11A through 11J. To use the aerosolization device 100 of FIGS. 11A through 11J, a user takes an assembled device, as shown in FIG. 11L, and removes the cap 500. Then, the user twists the endpiece 515 to cause the interior threads on the endpiece 515 to be separated from the exterior threads on the body 505 to disconnect the endpiece 515 from the body 505, thereby providing access to the chamber 115 so that the user may insert a capsule containing a pharmaceutical formulation. After insertion, the endpiece 515 is connected to the body by threaded engagement and the puncturing mechanism 525 is advanced to create one or more openings into the capsule. The user then places his or her mouth or nose on the endpiece 515 and inhales through the endpiece 515. The inhalation causes air to flow through the inlets 510 and into the chamber 115 where it causes the capsule to be swirled in a manner which causes the pharmaceutical formulation to be aerosolized. The aerosolized pharmaceutical formulation then flows through the endpiece and into the user's respiratory tract. The twist attachment of the endpiece 515 to the body 505 prevents the inadvertent disconnection of the endpiece 515 as a result of inhalation pressure and thereby reduces the risk of inhalation of the endpiece 515.

In a preferred version, the invention provides a system and method for aerosolizing a pharmaceutical formulation and delivering the pharmaceutical formulation to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperatures (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers. The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), both of which are incorporated herein by reference in their entireties. "Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a dry powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Therefore, the appended claims should not be limited to the description of the preferred versions contained herein and should include all such alterations, permutations, and equivalents as fall within the true spirit and scope of the present invention.

What is claimed is:

1. An aerosolization apparatus comprising:
   a body having an inlet;

an endpiece having an outlet, the endpiece being connectable to the body to define a chamber, wherein the chamber is sized to receive a capsule containing a pharmaceutical formulation in a manner which allows the capsule to move within the chamber and wherein the inlet is shaped to provide a swirling air flow in the chamber;

a connection mechanism comprising engageable threads to provide selective connection of the endpiece to the body, wherein a rotational force between the endpiece and the body is needed to connect and to disconnect the endpiece from the body, the rotational force being applied about an axis passing through the chamber, wherein the endpiece may be disconnected from the body to allow for insertion or removal of the capsule, and wherein the threads extend for less than two complete turns around the body;

a cap insertable over the endpiece and which covers at least a portion of the inlet when the endpiece is connected to the body, wherein the cap is connectable to the body by a press fit arrangement; and a puncturing mechanism capable of providing an opening in the capsule;

whereby when a user inhales, air enters into the chamber through the inlet so that the pharmaceutical formulation is aerosolized within the chamber and the aerosolized pharmaceutical formulation is delivered to the user through the outlet.

2. An aerosolization apparatus according to claim 1 wherein the body has a plurality of inlets.

3. An aerosolization apparatus according to claim 1 wherein the connection mechanism comprises engageable threads having a thread angle of less than about 9 degrees.

4. An aerosolization apparatus according to claim 1 wherein the connection mechanism comprises engageable threads having a thread angle of less than about 7 degrees.

5. An aerosolization apparatus according to claim 1 wherein the connection mechanism comprises engageable threads and wherein the threads include a recessed portion.

6. An aerosolization apparatus according to claim 1 wherein the connection mechanism comprises engageable threads and wherein the threads include a recessed portion that is recessed at an angle of less than about 75 degrees.

7. An aerosolization apparatus according to claim 1 wherein the puncturing mechanism is adapted to puncture a single end of the capsule.

8. An apparatus according to claim 1 wherein the chamber is elongated and has a longitudinal axis, and wherein the longitudinal axis of the chamber and the longitudinal axis of the capsule form an angle of less than about 45 degrees during use.

9. An apparatus according to claim 1 wherein the chamber is elongated and wherein the capsule is received lengthwise within the elongated chamber.

10. An aerosolization apparatus according to claim 1 wherein the width of the chamber is less than the length of the capsule.

11. An aerosolization apparatus according to claim 1 further comprising the capsule containing the pharmaceutical formulation and wherein the pharmaceutical formulation comprises an antibiotic.

12. An aerosolization apparatus according to claim 11 wherein the antibiotic comprises an aminoglycoside.

13. An aerosolization apparatus according to claim 12 wherein the aminoglycoside comprises tobramycin.

14. An aerosolization apparatus according to claim 11 wherein the antibiotic comprises a fluoroquinolone.

15. An aerosolization apparatus according to claim 14 wherein the fluoroquinolone comprises ciprofloxacin.

16. An aerosolization apparatus comprising:

a body having an inlet;

an endpiece having an outlet, the endpiece being connectable to the body to define a chamber, wherein the chamber is sized to receive a capsule containing a pharmaceutical formulation in a manner which allows the capsule to move within the chamber and wherein the inlet is shaped to provide a swirling air flow in the chamber;

a cap that is insertable over the endpiece and that covers at least a portion of the inlet when the endpiece is connected to the body, wherein the cap is connectable to the body by a press fit arrangement;

a connection mechanism to provide selective connection of the endpiece to the body, wherein the connection mechanism comprises engageable threads, and wherein the endpiece may be disconnected from the body to allow for insertion or removal of the capsule; and a puncturing mechanism capable of providing an opening in the capsule;

whereby when a user inhales, air enters into the chamber through the inlet so that the pharmaceutical formulation is aerosolized within the chamber and the aerosolized pharmaceutical formulation is delivered to the user through the outlet.

17. An aerosolization apparatus according to claim 16 wherein the engageable threads have a thread angle of less than about 9 degrees.

18. An aerosolization apparatus according to claim 16 wherein the engageable threads have a thread angle of less than about 7 degrees.

19. An aerosolization apparatus according to claim 16 wherein the engageable threads include a recessed portion.

20. An aerosolization apparatus according to claim 16 wherein the engageable threads include a recessed portion that is recessed at an angle of less than about 75 degrees.

21. An aerosolization apparatus according to claim 16 further comprising the capsule containing the pharmaceutical formulation and wherein the pharmaceutical formulation comprises an antibiotic.

22. An aerosolization apparatus according to claim 21 wherein the antibiotic comprises an aminoglycoside.

23. An aerosolization apparatus according to claim 22 wherein the aminoglycoside comprises tobramycin.

24. An aerosolization apparatus according to claim 21 wherein the antibiotic comprises a fluoroquinolone.

25. An aerosolization apparatus according to claim 24 wherein the fluoroquinolone comprises ciprofloxacin.

26. An aerosolization apparatus according to claim 16 wherein the cap is threadless.

27. A method of providing an aerosolized pharmaceutical formulation, the method comprising:

providing a body having an inlet and providing an endpiece having an outlet, the endpiece and the body having engageable threads that extend less than two complete turns, the endpiece being connectable to and disconnectable from the body when a rotational force is applied thereto to define a chamber, the chamber being sized to receive a capsule containing a pharmaceutical formulation, wherein the rotational force is applied about an axis that passes through the chamber, and wherein the endpiece may be disconnected from the body to allow for insertion or removal of the capsule;

providing a cap that may be removed from the endpiece by disconnecting a press fit arrangement to expose the inlet; and aerosolizing the pharmaceutical formulation when a user inhales by causing air to flow through an inlet in the body, within the chamber, and through an outlet in the endpiece to provide the aerosolized pharmaceutical formulation to the user and wherein the inlet is shaped to provide a swirling air flow in the chamber.

28. A method according to claim 27 wherein the threads have a thread angle of less than about 7 degrees.

29. A method according to claim 27 wherein the threads have a recessed portion.

30. A method according to claim 27 wherein the pharmaceutical formulation comprises a dry powder.

31. A method of aerosolizing a pharmaceutical formulation, the method comprising:

removing a cap from an endpiece by disconnecting a press fit arrangement to exposed an inlet;

rotating the endpiece relative to a body to expose a chamber in the body, wherein the body contains the inlet;

inserting a capsule containing a pharmaceutical formulation into the chamber in the body;

thereafter, rotating the endpiece relative to the body to connect the endpiece to the body, the rotation being about an axis passing through the chamber;

before, during, or after inserting the capsule into the chamber, providing an opening in the capsule;

inhaling through an opening in the endpiece to cause air to flow into the chamber through an inlet in the body thereby aerosolizing the pharmaceutical formulation, wherein the flow of air through the inlet causes a swirling flow in the chamber.

32. A method according to claim 31 wherein the chamber is elongated and wherein the capsule is inserted lengthwise into the elongated chamber.

33. A method according to claim 31 wherein the flow of air is through a plurality of inlets in the body.

34. A method according to claim 31 wherein the flow of air is through a plurality of inlets in the body.

35. A method of aerosolizing a pharmaceutical formulation, the method comprising:

inserting a capsule containing a pharmaceutical formulation into a chamber in a body;

thereafter, rotating an endpiece relative to the body to connect the endpiece to the body by engageable threads, the rotation being about an axis passing through the chamber and complete rotation being less than two turns;

before, during, or after inserting the capsule into the chamber, providing an opening in the capsule;

inhaling through an opening in the endpiece to cause air to flow into the chamber through an inlet in the body thereby aerosolizing the pharmaceutical formulation, wherein the flow of air through the inlet causes a swirling flow in the chamber; and thereafter, rotating the endpiece relative to the body to disconnect the endpiece from the body and expose the chamber;

thereafter, rotating the endpiece relative to the body to reconnect the endpiece to the body; and thereafter, installing a cap over the endpiece to cover at least a portion of the in inlet by connecting the cap to the body by a press fit arrangement.

\* \* \* \* \*